United States Patent [19]

Serres et al.

[11] Patent Number: 5,240,839
[45] Date of Patent: Aug. 31, 1993

[54] PARTICLE-MEDIATED TRANSFORMATION OF PERENNIAL FRUIT PLANTS CAPABLE OF ADVENTITIOUS BUDDING ON MICROPROPAGATED TISSUE

[76] Inventors: Rodney A. Serres, 2924 Harvey; Brent H. McCown, 236 E. Sunset Ct., both of Madison, Wis. 53705; Dennis E. McCabe, 8777 Airport Rd., Middleton, Wis. 53562

[21] Appl. No.: 622,672

[22] Filed: Dec. 5, 1990

[51] Int. Cl.[5] .......................... C12N 15/00; C12N 5/00
[52] U.S. Cl. ............................ 435/172.3; 435/240.45; 435/240.54; 935/67
[58] Field of Search ............ 435/172.3, 240.45, 240.49, 435/240.51, 240.54

[56] References Cited

PUBLICATIONS

Chevreau et al. 1987. Plant Cell Reports 7: 688–691.
Chalupa, V. 1988. Biol. Plant. 30(6): 414–421.
Serres et al. 1990. HortScience 25(9): 1130.
Scorza et al. 1984. HortScience 19(1): 66–68.
Lyrene, P. 1980. HortScience 15(1): 80–81.
Norton et al. 1985. Sci. Hortic. 27(3–4): 335–340.
Graham et al., "Use of the GUS Gene as a Selectable Marker for Agrobacterium-mediated Transformation of Rubus," *Plant Cell, Tissue and Organ Culture* 20: 35–39 (1990).
McGranahan et al., "Agrobacterium-mediated Transformation of Walnut Somatic Embryos and Regeneration of Transgenic Plants," *Biotechnology* 6: 800–804 (1988).
Dweikat, I. M. and Lyrene, P. M., "Adventitious Shoot Production From Leaves of Blueberry Cultured In Vitro," *HortScience* 23(3): 629 (1988).
Callow et al., "In Vitro Shoot Regeneration on Leaf Tissue from Micropropagated Highbush Blueberry," *HortScience*, 24[2]: 373–375 (1989).
McNicol, C. J. and Graham, J., "In Vitro Regeneration of Rubus from Leaf and Stem Segments," *Plant Cell, Tissue and Organ Culture*, 21: 45–50 (1990).
Nehra et al., "Direct Shoot Regeneration from Strawberry Leaf Disks," *J. Amer. Soc. Hort., Sci.*, 114[6]: 1014–1018 (1989).
Billings et al., "Regeneration of Blueberry Plantlets from Leaf Segments," *HortScience*, 23[4]: 763–766 (1988).
McCabe et al., "Stable Transformation of Soybean (Glycine Max) by Particle Acceleration," *Bio/Technology* 6: 923–926 (1988).
Klein et al., "Stable Genetic Transformation of Intact Nicotiana Cells by the Particle Bombardment Process," *Proc. Natl. Acad. Sci. USA*, 85:8502–8505 (1988).
Serres et al., "Genetic Transformation of Cranberry: Tissue Pretreatment and Selection," Presented at Jun. 13, 1990 TCA Meeting, Houston, Texas.
Flaherty, M. "Gene Fights Cranberry Pests," *Wisconsin State Journal*, Aug. 29, 1990, p. 8B.

*Primary Examiner*—David T. Fox
*Attorney, Agent, or Firm*—Quarles & Brady

[57] ABSTRACT

Cranberry has been genetically engineered using a particle mediated transformation procedure. The tissues transformed were nodes from which adventitious buds were induced. A flooding technique using the antibiotic kanamycin was used to select for transformants while limiting escapes. A gene for the toxin from *Bacillus thuringiensis* was introduced into the transgenic cranberry to confer insect toxicity.

12 Claims, 2 Drawing Sheets

FIG. 3

PARTICLE-MEDIATED TRANSFORMATION OF PERENNIAL FRUIT PLANTS CAPABLE OF ADVENTITIOUS BUDDING ON MICROPROPAGATED TISSUE

FIELD OF THE INVENTION

The present invention relates in general to the genetic engineering of plants, and relates, in particular, to particle-mediated transformation of perennial fruit plants capable of adventitious budding on micropropagated tissue.

BACKGROUND

The technology of recombinant DNA manipulation and insertion has evolved to the point where it is now possible to genetically engineer many crop plants. In the genetic engineering of crop plants, an exogenous genetic construction is inserted into the genomic DNA of the target plant species. The transformed plants can then express the exogenous gene product encoded by the genetic construction. If germ-line cells are transformed, the plants produced through such a process carry in their genomic DNA the inserted foreign genetic construction, which can thereafter be passed on to the progeny of the plant by normal plant breeding techniques. Using such techniques, it has become commonplace to genetically engineer model species, such as tobacco, petunia, carrot, potato and poplar. The techniques of genetic engineering have recently been extended to the important crop species cotton and soybean. Progress in plant genetic engineering has thus varied from crop plant family to family and the transformation of many species and families is yet to be demonstrated.

The most common technique utilized to transfer foreign genetic materials into plant cells makes use of the common soil-dwelling bacterium, *Agrobacterium tumefaciens*. *A. tumefaciens* is a plant pathogen that natively harbors a plasmid, referred to as the Ti (tumor-inducing) plasmid, which has the inherent ability to transfer a portion of its DNA (T-DNA) into a target plant cell. By suitable manipulation of the Ti plasmids of *Agrobacterium tumefaciens*, it is possible to insert a foreign genetic construction into the T-DNA of the Ti plasmid, which is then transformed into susceptible plant cells in tissue culture.

One difficulty in the utilization of Agrobacterium-mediated techniques for perennial fruit plant transformation is that Agrobacterium is very dependent on a species specific interaction between Agrobacterium and the cells of the target species plant. Another difficulty is that not all plant species can yet be regenerated from tissue cultures transformed by Agrobacterium. Cranberry, for example, has not been successfully transformed by Agrobacterium. Other perennial fruits, such as Rubus, have been transformed with Agrobacterium, Graham, J. et al., *Plant Cell Tissue Organ Culture* 20: 35-39 (1990).

Other techniques for transforming individual cells or cells in tissue culture include direct DNA injection and electroporation of plant protoplast cells. One especially promising alternative method for genetically engineering whole plants involves the coating of DNA or RNA onto small particles which are then physically accelerated into the cells of the target plant tissues, Klein et al., *Proc. Natl. Acad. Sci. U.S.A.*, 88: 8502-8505 (1988). A technique for germline transformation of soybean by particle-mediated transformation has been published, McCabe et al., *Bio/Technology*, 6: 923-926 (1988).

Genetic transformation of perennial fruits would permit expression of beneficial genes, such as the *Bacillus thuringiensis* crystal protein (B.t.) gene, which could potentially confer lepidopteran insect resistance. Vaeck, et al., (*Nature* 238: 33-37 (1987)) discuss insect-resistant plants that had been transformed with the B.t. gene. This toxin has been previously found to be specific to Lepidopteran insects, i.e., the larvae of moths and butterflies. Since caterpillars are a consumer of perennial fruits, the creation of plants having resistance to attack by Lepidopteran larvae would be of significant value.

Cranberry is a good example of a perennial fruit plant that could be beneficially genetically engineered. The American cranberry, *Vaccinium macrocarpon* Ait., is a woody, low-growing perennial vine. It is native to North America and found growing in temperate lowland marsh areas where the soil is acidic and high in organic matter. Cranberries are cultivated for their tart berries, which are primarily used for juice and sauce products. Cranberries, like most perennial fruits, are asexually propagated.

Cranberry marsh productivity has increased steadily over the years. Improvements in cultural practices have included the use of integrated pest management. However, problems such as insect and weed control are still prevalent, and control of these pests has been estimated to make up 45% of the growers, direct field costs. Currently, substantial amounts of carbamate and organophosphate insecticides are used throughout the growing season for insect control (Mahr et. al., *Cranberry Pest Control in Wisconsin*, University of Wisconsin—Extension Service Bulletin #A3276, p18, (1988)). Use of these insecticides poses problems of effectiveness and toxicity.

What is lacking in the art is an efficient, economical and rapid method of transforming cranberry and other perennial fruit plants capable of micropropagation and capable of adventitious budding on micropropagated tissue.

SUMMARY OF THE INVENTION

The present invention is a method of transforming perennial fruit plants capable of micropropagation and capable of adventitious budding on micropropagated tissue.

First, tissue is excised from a perennial fruit plant. Any plant tissue capable of micropropagation and adventitious budding may be used. This tissue is cultured and adventitious buds are induced on the cultured tissue.

Second, a genetic construct is created. Copies of the construct are made if the construct is of an isolated gene or genes. If the construct is a population of molecules, an amount of nucleic acid sufficient to effect transformation is isolated. The construct is coated onto small carrier particles.

Third, the cultured tissue with adventitious buds is placed on a target surface and bombarded with the nucleic acid-coated particles in an apparatus that provides an electric spark discharge in proximity to the particles. The acceleration of the carrier particles is determined by the voltage of the electric spark discharge.

Finally, plants are regenerated from the transformants. Either the regenerated whole plant or bombarded plant tissue may be assayed for the presence of the genetic construction.

It is an object of the present invention to genetically engineer perennial fruit plants.

It is another object of the present invention to genetically engineer cranberry plants.

It is an advantage of the present invention that whole perennial fruit plants can be regenerated from transformed tissue.

It is another advantage of the present invention that perennial fruit plants can be transformed in a rapid and efficient manner.

Other objects, advantages, and features of the present invention will become apparent from the following specification when taken in conjunction with the accompanying drawings.

BRIEF DESCRIPTION OF THE DRAWINGS

FIG. 3 is an illustration of a restriction map of the plasmid pTVBTGUS.

DESCRIPTION OF THE INVENTION

1. In General

Figure 1:
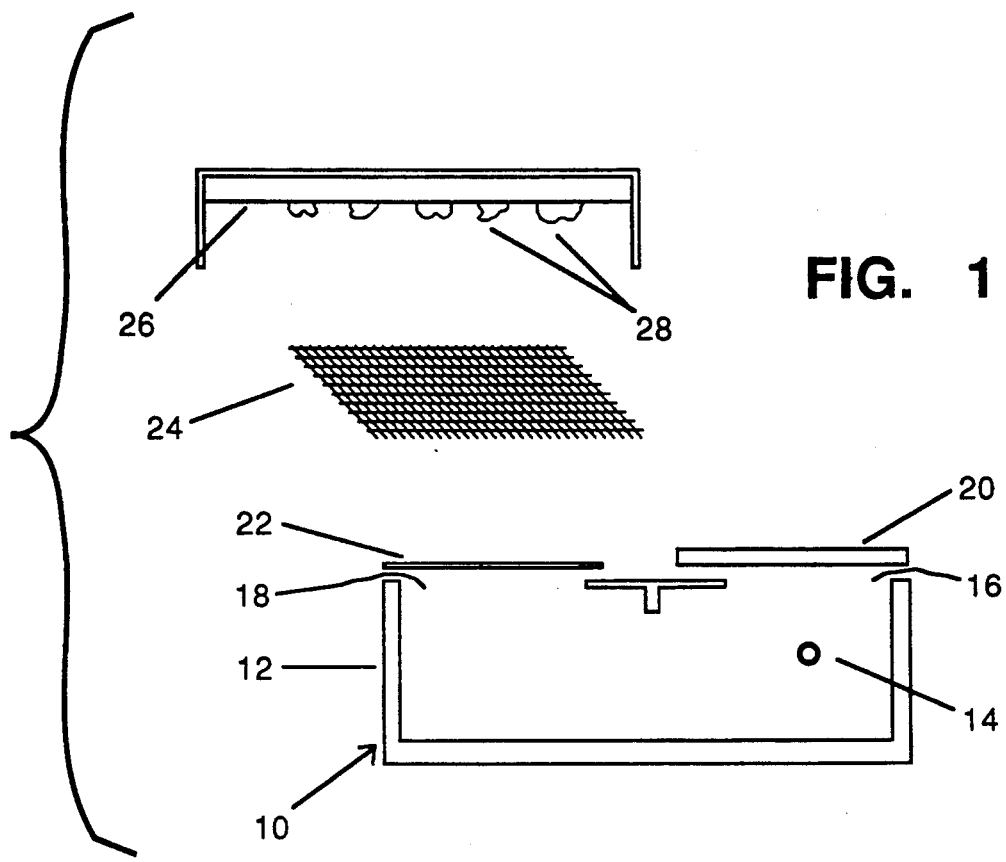
FIG. 1 is a side view of a particle acceleration apparatus useful within the procedure of the present invention.

The present invention is a process directed to the introduction of an exogenous genetic construction into the cells of a perennial fruit plant. Plants suitable for use in the present invention are capable of micropropagation and capable of producing adventitious buds from micropropagated tissue. Because such plants can be propagated asexually, it is not necessary that germ-line cells be transformed, only that vegetative tissue be transformed. The term "perennial fruit" refers to fruit plants that do not have to be replanted each year, but can be maintained from year to year.

Adventitious buds are shoots that have been induced in culture to form on somatic plant tissue, such as leaf or stem. Micropropagation and adventitious bud systems have been developed for several perennial fruit plants. Callow, et al., *Hort Science* 24(2): 373–375 (1989), report adventitious bud formation on leaf tissue from micropropagated highbush blueberry. Billings et al., *Hort Science* 23(4): 763–766 (1988), report a procedure to regenerate Berkeley and Bluehaven blueberry from leaf sections. Nehra and Stushnoff, *J. Amer. Soc. Hort. Sci.* 114(6): 1014–1018 (1989), report shoot regeneration from strawberry leaf disks. McNicol and Graham, *Plant Cell, Tissue and Organ Culture* 21: 45–50 (1990), report the regeneration of red raspberry, blackberry - raspberry hybrids, and blackberry from leaf and stem segments.

The technique of the present invention is demonstrated below with cranberry, *Vaccinium macrocarpon*, Ait. The technique may also be used on other closely related berry and horticultural crops which are amenable to similar manipulation in tissue culture and asexual reproduction. These amenable plants include members of the family Ericaceae, including Rhododendron species, such as rhododendron and azalea, other Vaccinium species, such as blueberry and huckleberry, and Kalmia species, such as Mountain laurel.

To summarize the invention briefly, the present process makes use of nucleic acid-coated particles which are propelled into perennial fruit plant cells to transform cells. In this process, first, tissue is excised from a perennial fruit plant and cultured in vitro. The tissue is induced to bud. Second, small carrier particles are coated with copies of a genetic construction. Third, the tissue with adventitious buds is bombarded with the nucleic acid-coated particles. Fourthly, the adventitious buds are subjected either to selection or to screening to identify transformant buds. The transformant buds may be asexually reproduced into whole plants carrying the inserted nucleic acid. Finally, the transformant buds are regenerated, and either the regenerated plant or the buds are assayed to verify the presence of the genetic construct.

2. Creation of the Genetic Construct

The genetic construct contains exogenous genetic material which may be derived from the same or a different species. The term "genetic construct" is meant to include artificial chimeric constructs of recombinant DNA or RNA molecules, as well as isolated genes in their native configuration.

If transformation of a particular gene is desired, the gene of interest must first be isolated. By standard molecular biological methods, the isolated gene is linked to regulatory elements that effectuate the expression of the gene. Preferably, these elements include a promoter sequence sufficient to initiate transcription and a terminator or polyadenylation signal sequence sufficient to terminate transcription. Translational and transcriptional enhancers may also be included. Typically, the gene and these elements are linked together on a plasmid or viral vector.

It is specifically envisioned that gene products other than proteins may be expressed by the genetic construction. For example, the inserted construction can express a negative RNA strand, also referred to as antisense RNA. The presence of this negative RNA strand may be desired to suppress the expression of an endogenous gene or to inhibit a disease process by a pathogenic organism.

3. Preparation of Plant Tissue for Transformation

Plant tissue is excised from the plant to be transformed. This tissue is called the "explant" and could be any plant tissue capable of adventitious bud formation. Examples of explants useful in the present invention include shoot or root tips, stems, leaves, root sections, embryos and germinated seedlings, although stem segments with single nodes are preferred. This explant tissue is disinfected and isolated on a medium that allows culturing. Preferably, woody plant medium (WPM) that additionally contains 0.13% calcium gluconate, 0.3% agar, 0.1% gelrite, 2% sucrose and 0.1 $\mu$M N-(3-methyl-2-butenyl)-1-H-purine-6-amine (2ip) is employed. WPM is defined by Lloyd and McCown in *Proc. Int. Plant Prop. Soc.* 30: 421–427 (1981). The tissue is transferred to fresh medium when needed. Typically, this is approximately every month.

In preparation for transformation, in vitro-cultured tissue is placed on a bud-inducing medium. One such medium is referred to here as "bud inducing medium," or BIM, which is WPM containing 10 $\mu$M 2ip, 1 $\mu$M thidiazuron (TDZ), 0.13% calcium gluconate, 0.3% agar, 0.1% gelrite and 2% sucrose. Conveniently, the medium may be contained in 60×15 mm disposable petri plates. The plant tissue remains on the BIM until adventitious buds appear. Typically in cranberry, this occurs in approximately fifteen days.

After BIM treatment and adventitious bud formation, the tissue is transferred to petri plates with fresh BIM containing compounds to inhibit microbial growth. The antibiotic carbenicillin (500 mg/L) and the fungicide benlate (150 mg/L) may be employed. This same petri dish may also serve as the target surface during transformation.

4. Transformation

Multiple copies of a genetic construction are prepared by suitable nucleic acid preparation techniques. The copies of the genetic construction, in aqueous solution, are then coated onto small particles of a durable, dense carrier material, such as gold. The carrier particles are typically in a size range of 1 to 3 microns.

Any of several methods may be used to join the nucleic acid construct to the carrier particles and then the carrier particles to the carrier sheet. The method used for the examples below was to suspend 2 microgram of DNA in 100 microliters of water with 100 microliters of spermidine (0.1M) and 100 microliters of polyethylene glycol (25%). Then 20 milligrams of gold carrier particles, of microcrystalline gold powder (Englehart) was introduced into the suspension. The suspension was then vortexed, and precipitated by the addition of 100 microliters of 2.5M $CaCl_2$. The precipitated complex was centrifuged and the supernatant was discarded. The precipitate were then resuspended in ethanol and coated onto a carrier sheet, upon which they may be air dried.

Figure 2:
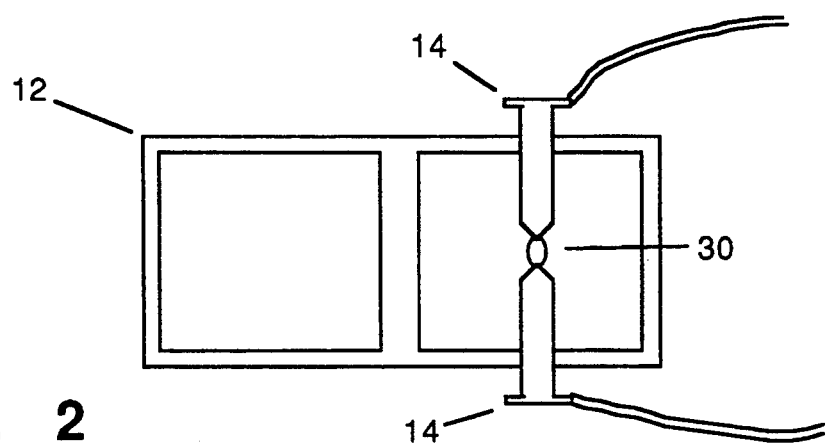
FIG. 2 is a top view of the same apparatus.

The process of the present invention is intended to make particular use of an apparatus utilizing an adjustable electric discharge device to physically accelerate nucleic acid-coated particles into plant cells. An apparatus suitable for use within the present invention is illustrated in FIGS. 1 and 2.

The apparatus consists of a spark discharge chamber 12 into which are inserted two electrodes 14 which are spaced apart by a distance of approximately 1 to 2 millimeters. The spark discharge chamber 12 is a horizontally extending rectangle having two openings 16 and 18 extending out its upward end. The opening 16 is covered by an access plate 20. The opening 18, located on the side of the rectangle of the spark discharge chamber 12 opposite from the electrodes 14, is intended to be covered by a carrier sheet 22. The electrodes 14 are connected to a suitable adjustable source of electric discharge voltage.

Such a source of electric discharge voltage would preferably include suitable electric switching connected to a capacitor of the one to two microfarad size range, with the amount of the voltage of the charge introduced onto the capacitor being adjustable, such as through the use of an autotransformer, through a range of perhaps 1 to 50,000 volts. Suitable high voltage electric switching (not shown) is provided so that the capacitor can safely be discharged through the electrodes 14 so that the apparatus can be used conveniently by a user.

The carrier sheet 22 intended to be placed upon the opening 18 in the spark discharge chamber 12 is a planar sheet of relatively stiff material. One example of a suitable material is aluminized saran coated mylar. Above the opening 18 in the discharge chamber 12, positioned approximately 5 to 10 millimeters above it, is a retaining screen 24. Placed approximately 5 to 25 millimeters above the retaining screen 24 is a target surface 26. The target surface 26 can be any suitable culture surface onto which the material to be transformed may readily be placed, such as an overturned petri dish into which the plant tissues have been positioned for culture.

The nucleic acid-coated particles are then placed upon the carrier sheet 22 which is inserted at the proper opening on the top of the spark discharge chamber 12. To this end, the ethanol suspension containing the nucleic acid-coated particles is pipetted onto the carrier sheet 22 in a uniform layer and allowed to settle for 30 seconds. After settling, the meniscus is broken and excess ethanol is drained away. Residual ethanol is removed by evaporation. Preferably, about 0.05 milligrams of coated gold carrier particles are layered per square centimeter of carrier sheet. The carrier sheet 22 is then inserted on top of the spark discharge chamber 12.

The target surface 26, including the living plant material thereon, is then placed in position above the retaining screen 24. A small droplet of water, preferably 2 to 4 microliters in size, is then placed bridging the ends of the electrodes 14. The access cover 20 is placed in position on top of the spark discharge chamber 12.

At this point the entire apparatus is enclosed in a vacuum chamber and a vacuum is drawn to the range of approximately 500 millimeters of mercury. A supply of helium is continuously bled into the vacuum chamber to replace the atmosphere in the space between the carrier sheet and the target. Helium has a lower relative density than the atmosphere it replaces, so the coated particles experience less drag when they are propelled toward the plant tissue.

A spark discharge is then initiated by the user between the electrodes 14. This is done by means of the appropriate electric switching which applies the voltage stored in the capacitor across the terminals of the electrodes 14. The electric discharge bridges the spark discharge gap between the electrodes 14 and instantly vaporizes the small droplet of water previously placed there. The force of vaporization creates a shock wave within the spark discharge chamber 12 which radiates outward in all directions. The impact of the radiating shock wave upon the carrier sheet 22 propels the carrier sheet 22 upward with great velocity. The upwardly traveling carrier sheet 22 accelerates until it contacts the retaining screen 24. The use of the helium within the vacuum containment for the apparatus provides less drag on the flight of the carrier sheet 22 as well as less force necessary for the shock wave to propagate the carrier particles to the target tissues.

At the retaining screen 24, the carrier sheet 22 is halted. The nucleic acid-coated particles fly off of the carrier sheet and travel freely onward toward the target tissues. The small carrier particles then proceed into the cells of the target tissues placed on the target surface 26 and pass freely into the cytosol of the tissue placed thereon.

The actual momentum of the carrier particles as they impact on the surface of the target tissues is adjustable, based upon the voltage of the initial electric discharge applied to the electrodes 14. By varying the amount of the electric discharge applied across the electrodes 14, the velocity by which the particles impact the target can be adjusted and, thus, the depth of penetration of the carrier particles into the tissue of the target tissues can be adjusted continuously throughout the range of adjustment provided for the electric voltage applied across the electrodes 14.

As will be apparent from the following examples, the technique of particle-mediated genetic transformation can be adapted to a wide variety of different plant types. The use of a tunable electric spark discharge for the motive force in the particle acceleration has proven also to be of great advantage, since the acceleration imparted to the particles can be readily and easily tuned using this technique, thereby facilitating adaptation of the technique to different plants.

5. Recovery of Transformed Plants

When plant tissues are subjected to a particle-mediated transformation event, even under optimal conditions, only a small fraction of the cells in the tissue subjected to the process will be transformed. It then becomes necessary to recover propagating plant tissues derived substantially or solely from those tissues. There are two broad approaches to surmounting this difficulty, screening and selection. Using a screening approach, large numbers of propagatable shoots are generated which are then screened by biochemical or phenotypical assay for the presence of the inserted DNA. Using the selection approach, a selectable marker gene is incorporated into the foreign genetic construct transformed into the plant cells, which are then subjected to a regimen of selection by an agent to which the selectable marker confers immunity. The selection approach is generally more efficient, but effective selection agents are not available for many plant varieties. In particular, a selection agent commonly used for Agrobacterium-mediated plant transformation protocols, kanamycin, has proven of limited value with some plant species, notably soybean and, until now, cranberry. A common problem with such a selection agent with these species is that there are too many "escapes," or regenerating plant buds which survive the selection regimen but which are not transformed. If there are large numbers of such escapes, it becomes difficult or even impractical to locate any transformants among the regenerating buds. If the selection agent is increased to such a level that escapes are prevented, all the plant tissues die.

Described below is a new regimen for a selection protocol that has proven effective in cranberry. It is based on a liquid overlay of kanamycin solution bathing the tissues placed on a semi-solid BIM medium for growth. This level of intense exposure to the selection agent proved effective to prevent an unacceptable level of escapes while preserving the viability of the transformed tissues, and thus provided a practical solution to this difficulty.

If, for some reason, selection was not to be used, a screening protocol could be used. Under a screening procedure, large numbers of shoots could be regenerated and then tested for the presence of a marker gene included in the transforming DNA. One such useful marker gene is the beta-glucuronidase (GUS) gene, the expression of which may readily be detected by a convenient colormetric assay.

Once transformant buds or shoots are identified, whole transgenic plants may be regenerated. The presence of the transforming DNA in the whole plant can be verified by biochemical analysis, conveniently performed by PCR procedures. From such a whole plant, conventional style cuttings can be taken to asexually propagate the plant, as is conventionally done with cranberry and other perennial fruit plant species.

EXAMPLE

Stem sections of the commonly used cranberry cultivar "Stevens" were excised from field-grown plants, disinfected, and isolated on WPM that additionally contained 0.13% calcium gluconate, 0.3% agar, 0.1% gelrite, 2% sucrose and 0.1 $\mu$M 2ip in Magenta GA7 boxes (Magenta Corp., Chicago). Nodal stem sections were transferred to fresh medium approximately every month. These cultures were maintained for one year to assure stabilization.

In preparation for transformation, in vitro-derived stems were divided into one-node stem sections approximately 5 mm long with the node at the distal end. These stem sections were placed on bud induction medium (BIM), which is WPM containing 10 $\mu$M 2ip, 1 $\mu$M thidiazuron (TDZ), 0.13% calcium gluconate, 0.3% agar, 0.1% gelrite, and 2% sucrose in 60×15 mm disposable petri plates. Treatment on this medium lasted for 15 days. Adventitious buds were visible after 14 days of culture.

After BIM treatment, the stem sections were transferred to a petri dish containing fresh BIM and the antibiotics carbenicillin (500 mg/L) and benlate (150 mg/L) for transformation. This petri dish serves as a transformation target surface. Approximately 25 dishes, each containing 10 stem sections, were bombarded by DNA-coated carrier particles.

Figure 3:
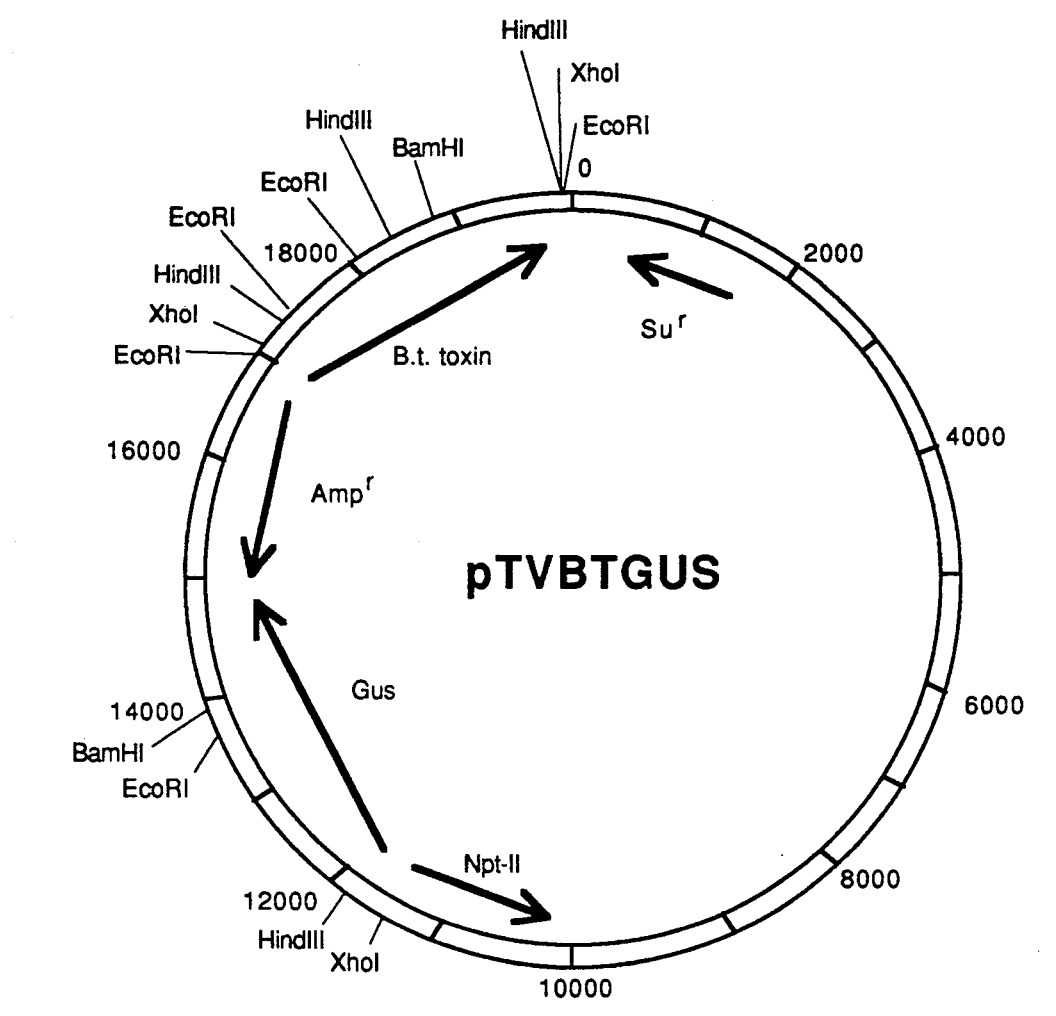

Transformation was accomplished using the apparatus described above. Microscopic gold particles coated with pTVBTGUS plasmid DNA containing the NPTII, GUS and B.t. genes bombarded the tissue. The NPTII gene encodes kanamycin resistance, the GUS gene encodes beta-glucuronidase, and the B.t. gene encodes the insect toxin produced by *Bacillus thuringiensis.* These genes were linked together in the plasmid pTVBTGUS, which is illustrated in FIG. 3. This plasmid was constructed and multiple copies obtained by standard molecular biological methods. The plasmid DNA was coated onto the particles at a rate of 0.1 microgram DNA per milligram of gold particles by the method described above. The coated carrier particles were placed on the carrier sheet at a rate of 0.05 mg per square cm. The voltage used to bombard the cranberry stems was 16 KV.

Forty-eight hours after bombardment, randomly selected stem sections were chosen for the B-glucuronidase histochemical assay that tests for expression of the GUS gene. This assay was by the method of Jefferson et al., *EMBO J* 6: 3901-3907 (1987). In brief, stem sections were transferred to single wells of a 24-well culture plate and bathed in the X-glucuronic acid reaction mixture for 24 hours at room temperature. After 24 hours, the reaction mixture was decanted and the stem sections were rinsed with sterile distilled water twice before being covered with lactophenol for clearing. The number of blue spots per stem section were then counted to determine transient transformation rates. Each assayed stem section contained blue cells, indicative of GUS transformation. Approximately 10 stem sections were assayed, and approximately 38 cells in each stem section were blue.

Bombarded stem sections not assayed for GUS were transferred to BIM containing 300 mg/L kanamycin in 100 ml baby food jars capped with Magenta B-caps for selection of transformed cells. Three weeks after bombardment, a 5 ml liquid overlay of 300 mg/L kanamycin was added to the surface of the solid medium. This overlay bathed, but did not entirely submerge, all of the stem sections.

Previous experiments not using a kanamycin overlay were hampered by the occurrence of escape tissue (rapidly dividing and developing nontransformed tissue) even at high (300 mg/L) levels of kanamycin in the solid medium. This indicates poor translocation of kanamycin through the cranberry tissue and the need for better contact of the tissue with the kanamycin. The liquid overlay provided the needed contact and inhibited growth of nontransformed tissue. The three week period prior to the overlay allowed recovery from bombardment and further development of the adventitious buds on the upper (bombarded) surface of the stem sections.

Three weeks after the overlay was applied, it was evident that nontransformed tissues had stopped normal growth at the time of the overlay while transformed shoots had continued to develop. Green bud masses and some elongating shoots with well-developed green leaves were evident amidst the masses of chlorotic tissues. Of the original 250 stem sections transformed, 11 survived antibiotic selection. Six weeks after bombardment, elongated putatively transformed shoots were isolated and grown on WPM+0.2 μM 2ip in GA7 boxes. The putatively transformed, elongated shoots were transferred to WPM+0.1 μM 2ip as they developed on this medium. Histochemical assays for GUS expression were performed on the selected shoots.

After several subcultures, small amounts of putatively transformed stem and leaf tissue were used for DNA extraction. Polymerase chain reaction (PCR) was performed to verify the presence of the three introduced genes. PCR analysis of putatively transformed shoots that had been carried through several subcultures showed the presence of all three genes, establishing proof of the recovery of stably transformed cranberry plants.

Expression of the GUS gene was verified through histochemical assays on selected shoots. Some shoots that were shown to contain the GUS gene by PCR did not give a positive histochemical reaction. Progeny analyses were not deemed necessary, since cranberry is commercially propagated strictly by vegetative means, and the presence and expression of the inserted genetic construct was confirmed by the PCR analysis and the GUS expression assay. Approximately 0.15% of the cells estimated as originally expressing the GUS gene resulted in recovered, transformed and expressing shoots that could be cultivated into plants. Such asexually propagating tissue and plants expressing the inserted gene will demonstrate the inserted phenotype.

Since the plasmid pTVBTGUS incorporates a gene coding for the B.t. toxin, the resulting cranberry plants express this toxin and will prove toxic, upon ingestion, to Lepidopteran insects. This gene has already been demonstrated to achieve this toxicity when inserted in tobacco, cotton, tomato, and poplar plants. Since Lepidopteran pests are significant problems in cranberry, the plants produced here are capable of reducing the need for pesticide application in cranberry cultivation.

Eleven of the plants transformed by this technique were recovered. All eleven exhibited phenotypic resistance to the antibiotic kanamycin compared to control plants. Of the eleven, eight gave a clear indication of GUS activity by histochemical assay, and the controls did not. DNA was recovered from nine of the eleven plants, and from controls, and subjected to a PCR analysis to detect the presence of the inserted DNA in the plants. The DNA coding for kanamycin resistance was detected in all nine plants while the genes coding for GUS and B.t. were detected in eight out of nine. None of the genes were detected in the controls. This suggests that occasional recombinant events or deletions are possible, but that recovery of phenotypically transgenic plants occurs at a very practical level of frequency.

It is to be understood that the present invention is not limited to the examples described here but embraces all such modified forms thereof as come within the following claim.

I claim:

1. A method of creating transgenic cranberry plants, comprising the steps of (a) excising stem tissue from a cranberry plant;
(b) culturing the stem tissue;
(c) inducing adventitious buds on the cultured tissue by treatment with a cytokinin;
(d) creating a genetic construction including a selectable marker gene encoding resistance to kanamycin;
(e) coating copies of the genetic construction onto carrier particles, the particles being of a sufficiently small size so as to be inserted into plant cells without killing the cells;
(f) placing the cultured tissue with adventitious buds on a target surface;
(g) accelerating the carrier particles such that the coated carrier particles bombard the target surface, so that coated carrier particles are introduced into the cells of the target tissue;
(h) culturing the bombarded cultured tissue with a liquid kanamycin overlay containing a sufficient amount of kanamycin so as to terminate most of the tissues which have not incorporated the genetic construction;
(i) regenerating whole plants from the transformants; and
(j) assaying either bombarded plant tissue or regenerated plants for the expression of the genetic construction.

2. A method as in claim 1 wherein the carrier particles are gold.

3. A method as in claim 1 wherein the excised tissue is cultured in WPM.

4. A method as in claim 1 wherein cultured tissue is incubated in BIM to induce adventitious budding.

5. A method as in claim 1 wherein the bombarded tissue is grown in WPM with 0.1 μM 2ip.

6. A method as in claim 1 wherein the explosive force in step (g) is from an adjustable electric spark discharge.

7. A method of creating transgenic cranberry plants, comprising the steps of (a) excising stem sections from the plant;
(b) culturing the stem sections;
(c) inducing adventitious buds on the cultured stem sections through the application of a cytokinin;
(d) creating a genetic construction including a selectable marker gene encoding resistance to kanamycin;
(e) coating copies of the genetic construction onto carrier particles, the particles being of a sufficiently small size so as to be inserted into cranberry cells without killing the cranberry cells;
(f) placing one or more of the cultured plant stem sections with adventitious buds on a target surface;
(g) initiating an explosive electric spark discharge in proximity to the carrier particles such that the coated carrier particles bombard the target surface so that coated carrier particles are introduced into the cells of the stem sections, the acceleration of the carrier particles being determined by the voltage of the electric spark discharge;

(h) culturing the stem sections in the presence of a selection agent in the form of a liquid kanamycin overlay so as to terminate most of the stem sections which have not incorporated the genetic construction;

(i) regenerating whole plants from the stem sections; and (j) assaying either the bombarded tissue or the regenerated plant for the presence of the genetic construction.

8. A method as in claim 7 wherein the excised stem sections were of nodal length.

9. A method as in claim 7 wherein the carrier particles are gold.

10. A method as in claim 7 wherein the excised stem sections are cultured in WPM.

11. A method as in claim 7 wherein stem sections were incubated in BIM to induce adventitious budding.

12. A method as in claim 7 wherein the bombarded stem sections are grown in WPM with 0.1 μM 2ip.

* * * * *